US009206268B2

(12) United States Patent
Link et al.

(10) Patent No.: US 9,206,268 B2
(45) Date of Patent: Dec. 8, 2015

(54) METHODS AND COMPOSITIONS FOR INHIBITING POLYSTYRENE FORMATION DURING STYRENE PRODUCTION

(75) Inventors: John Link, Humble, TX (US); Mike Hong, Shanghai (CN)

(73) Assignee: General Electric Company, Schenectady, NY (US)

( * ) Notice: Subject to any disclaimer, the term of this patent is extended or adjusted under 35 U.S.C. 154(b) by 992 days.

(21) Appl. No.: 13/235,004

(22) Filed: Sep. 16, 2011

(65) Prior Publication Data

US 2013/0072729 A1 Mar. 21, 2013

(51) Int. Cl.
*C08F 12/08* (2006.01)
*C08F 2/40* (2006.01)
*C07C 7/20* (2006.01)
*C07C 17/42* (2006.01)
*C09K 3/00* (2006.01)

(52) U.S. Cl.
CPC . *C08F 12/08* (2013.01); *C07C 7/20* (2013.01); *C07C 17/42* (2013.01)

(58) Field of Classification Search
None
See application file for complete search history.

(56) References Cited

U.S. PATENT DOCUMENTS

| 3,821,304 | A | 6/1974 | Klemchuk | |
|---|---|---|---|---|
| 4,032,547 | A | 6/1977 | Bacha et al. | |
| 4,929,778 | A | 5/1990 | Roling | |
| 5,254,760 | A | 10/1993 | Winter et al. | |
| 5,470,440 | A | 11/1995 | Arhancet | |
| 5,489,718 | A | 2/1996 | Arhancet | |
| 5,562,863 | A | 10/1996 | Arhancet | |
| 5,616,774 | A | 4/1997 | Evans et al. | |
| 6,024,894 | A | 2/2000 | Arhancet | |
| 6,143,205 | A | 11/2000 | Sutoris et al. | |
| 6,344,560 | B1 * | 2/2002 | Geelan et al. | 546/21 |
| 6,388,155 | B1 | 5/2002 | Sy et al. | |
| 6,403,850 | B1 * | 6/2002 | Benage et al. | 585/5 |
| 6,447,649 | B1 | 9/2002 | Arhancet | |
| 6,926,820 | B2 | 8/2005 | Eldin et al. | |
| 7,128,826 | B2 | 10/2006 | Eldin et al. | |
| 7,743,809 | B2 * | 6/2010 | Seo | 156/497 |
| 8,901,362 | B2 * | 12/2014 | Link | 585/2 |
| 2005/0113626 | A1 * | 5/2005 | Benage et al. | 585/950 |
| 2006/0069219 | A1 * | 3/2006 | Kosover et al. | 526/82 |
| 2006/0167244 | A1 | 7/2006 | Philips et al. | |
| 2010/0093897 | A1 * | 4/2010 | Benage et al. | 524/87 |
| 2013/0072729 | A1 * | 3/2013 | Link et al. | 585/4 |
| 2013/0204053 | A1 * | 8/2013 | Link | 585/2 |

FOREIGN PATENT DOCUMENTS

JP 2006182718 7/2006
WO 2012004605 A1 1/2012

OTHER PUBLICATIONS

Search Report and Written Opinion from corresponding PCT Application No. PCT/US2012/050511 dated Sep. 19, 2012.
Tummatorn et al., "A Convergent General Strategy for the Functionalized 2-Aryl Cycloalkyl-Fused Chromans: Intramolecular Hetero-Diels-Alder Reactions of ortho-Quinone Methides", Communication, Chem. Eur. J., vol. 16, pp. 1445-1448, 2010.

* cited by examiner

*Primary Examiner* — Joseph D Anthony
(74) *Attorney, Agent, or Firm* — Wegman, Hessler & Vanderburg

(57) ABSTRACT

Methods and compositions are provided for inhibiting the polymerization of a vinyl aromatic monomer, such as styrene monomer, during elevated temperature processing or distillation thereof. The compositions comprise an inhibitor combination of (A) a hydroxylamine and (B) a stable free radical plus a retarder that is either; (C) dinitrobutylphenol or (D) quinone methide. The ratio of (A) to (B) ranges from about 5% (A) to 95% (B) to about 95% (A) to about 5% (B). The compositions are added to the vinyl aromatic monomer in amounts sufficient to prevent polymerization during the distillation process. Typically the inhibitor combination is added to the vinyl aromatic monomer in an amount ranging from about 10 to 150 ppm of the monomer. Retarders are typically added in an amount ranging from 50 to 1500 ppm of the vinyl aromatic monomer.

10 Claims, No Drawings

METHODS AND COMPOSITIONS FOR INHIBITING POLYSTYRENE FORMATION DURING STYRENE PRODUCTION

FIELD OF INVENTION

The invention pertains to methods and compositions for inhibiting polymerization of a vinyl aromatic monomer, such as styrene monomer, during the purification or distillation step of the production process.

BACKGROUND OF THE INVENTION

Common industrial methods for producing styrene typically include separation and purification processes, such as distillation, to remove unwanted impurities. Unfortunately, purification processes carried out at elevated temperatures result in an increased rate of undesired polymerization. Heat polymerization is rapid. This polymerization is undesirable during many stages of the manufacturing and processing of styrene monomers, as it results not only in a loss of the desired monomer end-product, but a loss of production efficiency caused by polymer formation and/or agglomeration of polymer on process equipment.

To minimize these losses, distillation is generally carried out under vacuum. In addition, inhibitors and retarders are frequently used. Inhibitors include hydroxylamines and stable free radicals. True inhibitors have a termination rate that is greater than 10 times the polymerization propagation rate. These inhibitors completely eliminate polymer formation for a period of time, known as the induction period. Retarders include dinitrobutylphenol and quinone methides. Retarders are not true inhibitors as their systems have no induction period and the termination to propagation rate is less than 10. Instead, retarders keep polymerization at a low, controlled rate.

Hydroxylamines work well at temperatures between 110° C. to 125° C., and stable free radicals work well at temperatures below 110° C. However, styrene is purified at temperatures that vary from one manufacturing plant to another. Moreover, temperatures will also vary with each distillation column at the same manufacturing plant. Thus, temperature ranges will vary from about 75° C. to 125° C. during the typical styrene distillation process, creating strong need for methods that reduce polymerization across the 75° C. to 125° C. temperature range.

SUMMARY OF THE INVENTION

There are three exemplary embodiments of the invention. In the first embodiment, a method is provided for inhibiting the polymerization of a vinyl aromatic monomer such as styrene monomer. The method comprises adding an effective polymerization inhibiting amount of a combined treatment, or composition, to the monomer medium just before the distillation process. The combined treatment comprises (A) a hydroxylamine and (B) a stable free radical with a ratio ranging from about 5% (A) to 95% (B) to about 95% (A) to about 5% (B). From about 10-150 ppm of (A) and (B) collectively is brought into contact with the requisite vinyl aromatic monomer based on 1 million parts of the monomer.

In the second embodiment of the invention, a vinyl aromatic monomer anti-polymerization composition is added to the monomer medium just before the distillation process. This composition includes the combined treatment of (A) a hydroxylamine and (B) a stable free radical, plus (C) a dinitrobutylphenol retarder. From about 10-150 ppm of (A) and (B) collectively is brought into contact with the requisite vinyl aromatic monomer based on 1 million parts of the monomer. From about 50 to 1500 ppm of the dinitrobutylphenol retarder is brought into contact with the vinyl aromatic monomer based on 1 million parts of the monomer.

In the third embodiment of the invention, a vinyl aromatic monomer anti-polymerization composition is added to the monomer medium just before the distillation process. This composition includes the combined treatment of (A) a hydroxylamine and (B) a stable free radical, plus (D) a quinone methide retarder. From about 10-150 ppm of (A) and (B) collectively is brought into contact with the requisite vinyl aromatic monomer based on 1 million parts of the monomer. From about 50 to 1500 ppm of the quinone methide retarder is brought into contact with the vinyl aromatic monomer based on 1 million parts of the monomer.

The present invention and its advantages over the prior art will become apparent upon reading the following detailed description and the appended claims.

DETAILED DESCRIPTION OF EXEMPLARY EMBODIMENTS

Approximating language, as used herein throughout the specification and claims, may be applied to modify any quantitative representation that could permissibly vary without resulting in a change in the basic function to which it is related. Accordingly, a value modified by a term or terms, such as "about", is not limited to the precise value specified. In at least some instances, the approximating language may correspond to the precision of an instrument for measuring the value. Range limitations may be combined and/or interchanged, and such ranges are identified and include all the sub-ranges stated herein unless context or language indicates otherwise. Other than in the operating examples or where otherwise indicated, all numbers or expressions referring to quantities of ingredients, reaction conditions and the like, used in the specification and the claims, are to be understood as modified in all instances by the term "about".

"Optional" or "optionally" means that the subsequently described event or circumstance may or may not occur, or that the subsequently identified material may or may not be present, and that the description includes instances where the event or circumstance occurs or where the material is present, and instances where the event or circumstance does not occur or the material is not present.

As used herein, the terms "comprises", "comprising", "includes", "including", "has", "having", or any other variation thereof, are intended to cover a non-exclusive inclusion. For example, a process, method, article or apparatus that comprises a list of elements is not necessarily limited to only those elements, but may include other elements not expressly listed or inherent to such process, method, article, or apparatus.

The singular forms "a", "an", and "the" include plural referents unless the context clearly dictates otherwise.

The methods of the present invention can control fouling caused by the polymerization of monomer on processing equipment used in the manufacturing of styrene monomer. The instant invention may be used as a process inhibitor, alone or with a retarder, which is employed during preparation and processing (e.g., employing heat) of the styrene monomer.

The invention will now be described in conjunction with the following examples which should be viewed as being illustrative of the invention and should not be deemed to limit the invention in any manner.

In accordance with the invention, a combined treatment comprising (A) a hydroxylamine and (B) a stable free radical are conjointly utilized to inhibit polymerization of a vinyl aromatic monomer such as styrene.

Hydroxylamines have the functional group —NOH— and the general formula $R_1$—NOH—$R_2$. $R_1$ and $R_2$ may be the same or different and are hydrogen, alkyl, aryl, alkaryl, or hydroxyalkyl groups and preferably have three to about twenty carbon atoms. At present, the preferred compound (A) is 2-propanol, 1,1'-(hydroxyimino)bis, or 1,1'-(hydroxyimino)dipropan-2-ol, or bis 1,1-(2-Propanol)-hydroxyimine.

In addition to the hydroxylamine, the combined treatment has a stable free radical. Stable free radicals include nitroxyl compounds. Among these nitroxyl compounds, the preferred compound (B) for the combined treatment is 4-hydroxy-2,2,6,6-tetramethyl-1-piperidinyloxy, or tetramethylpiperidino-N-oxyl, or 1-oxyl-2,2,6,6-tetramethyl-4-piperidinol.

In accordance with the invention, suitable retarders include dinitrobutylphenol (C) and quinone methide (D). The quinone methide (QM) compound has the formula:

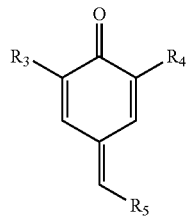

wherein $R_3$ and $R_4$ are independently H, $C_1$ to $C_{18}$ alkyl, $C_5$ to $C_{12}$ cycloalkyl; or $C_7$ to $C_{15}$ phenylalkyl, and $R_5$ is aryl, or aryl substituted with $C_1$ to $C_6$ alkyl, alkoxy, hydroxy, nitro, amino, carboxy or mixtures thereof.

The compositions of the present invention are effective at inhibiting polymerization of vinyl aromatic monomers under processing conditions. These processing conditions include but are not limited to preparation, purification, distillation and vacuum distillation processes.

Styrene, for example, is typically processed at temperatures between 75° C. and 125° C. The compositions of the present invention are effective at inhibiting the polymerization of styrene over this range of temperatures.

The vinyl aromatic monomers that are treated by the compositions of the present invention include but are not limited to styrene, bromostyrene, divinylbenzene, and α-methylstyrene. The compositions of the present invention are particularly efficacious at inhibiting and/or retarding the polymerization of styrene monomer.

The total amount of hydroxylamine (A) and stable free radical (B) and dinitrobutylphenol (C) or quinone methide (D) used in the methods of the present invention is that amount which is sufficient to inhibit polymerization of vinyl aromatic monomers. This amount will vary according to the conditions under which the vinyl aromatic monomer is being processed, contaminants in the system, and the temperature of the system. At higher processing temperatures and higher monomer contamination, larger amounts of the inhibiting composition are required.

Accordingly, it is possible to create a more robust method of inhibiting vinyl aromatic monomer polymerization than is obtained by the use of either a hydroxylamine or stable free radical by itself. This method works well in both the low and high temperature zones of styrene distillation thus lowering the total amount of polymerization. For purposes of the present invention, the term "effective inhibiting amount" is that amount which is effective at inhibiting vinyl aromatic monomer polymerization.

The compositions of the present invention can be introduced into the vinyl aromatic monomer by any conventional method at any point of the processing system, either as separate and individual ingredients or as a combination of ingredients. Preferably, the compositions are added just before the styrene purification or distillation process.

The compositions of the present invention may be added to the vinyl aromatic monomer as a solution using a suitable liquid carrier or solvent. Any solvent that is compatible with the individual ingredients of the composition and the vinyl aromatic monomer to be treated may be employed. It is often desirable to dissolve the inhibitors in the monomer to which the inhibitor is being added to avoid introducing additional impurities in the monomer. Exemplary liquid carriers include water and non-polar organic solvents, such as ethyl benzene.

In accordance with the invention, both a hydroxylamine (A) and a stable free radical (B) are combined to inhibit polymerization of a vinyl aromatic monomer such as styrene. An effective polymerization inhibiting amount of a combined treatment, or composition, is added to the monomer medium just before the distillation process. The combined treatment comprises (A) to (B) with a ratio ranging from about 5% (A) to 95% (B) to about 95% (A) to about 5% (B). From about 10-150 ppm of (A) and (B) collectively is brought into contact with the requisite vinyl aromatic monomer based on 1 million parts of the monomer.

In another embodiment of the invention, a vinyl aromatic monomer anti-polymerization composition is added to the monomer medium just before the distillation process. This composition includes the combined treatment of (A) a hydroxylamine and (B) a stable free radical, plus (C) a dinitrobutylphenol retarder. From about 10-150 ppm of (A) and (B) collectively is brought into contact with the requisite vinyl aromatic monomer based on 1 million parts of the monomer. From about 50 to 1500 ppm of the dinitrobutylphenol retarder is brought into contact with the vinyl aromatic monomer based on 1 million parts of the monomer.

In a third embodiment of the invention, a vinyl aromatic monomer anti-polymerization composition is added to the monomer medium just before the distillation process. This composition includes the combined treatment of (A) a hydroxylamine and (B) a stable free radical, plus (D) a quinone methide retarder. From about 10-150 ppm of (A) and (B) collectively is brought into contact with the requisite vinyl aromatic monomer based on 1 million parts of the monomer. From about 50 to 1500 ppm of the quinone methide retarder is brought into contact with the vinyl aromatic monomer based on 1 million parts of the monomer.

While this invention has been described in conjunction with the specific embodiments described above, it is evident that many alternatives, combinations, modifications and variations are apparent to those skilled in the art. Accordingly, the preferred embodiments of this invention, as set forth above are intended to be illustrative only, and not in a limiting sense. Various changes can be made without departing from the spirit and scope of this invention. Therefore, the technical scope of the present invention encompasses not only those embodiments described above, but also all that fall within the scope of the appended claims.

This written description uses examples to disclose the invention, including the best mode, and also to enable any person skilled in the art to practice the invention, including making and using any devices or systems and performing any incorporated processes. The patentable scope of the invention is defined by the claims, and may include other examples that occur to those skilled in the art. These other examples are intended to be within the scope of the claims if they have structural elements that do not differ from the literal language of the claims, or if they include equivalent structural elements with insubstantial differences from the literal language of the claims.

What is claimed is:

1. A vinyl aromatic monomer anti-polymerization composition comprising (A) 2-propanol 1,1'-(hydroxyimino)bis and B) a nitroxyl free radical compound.

2. The vinyl aromatic monomer anti-polymerization composition of claim 1, wherein the ratio of (A) to (B) ranges from about 5% (A) to 95% (B) to about 95% (A) to about 5% (B).

3. The vinyl aromatic monomer anti-polymerization composition of claim 1, wherein the nitroxyl free radical compound (B) is a member selected from the group consisting of 4-hydroxy-2,2,6,6-tetramethyl-1-piperidinyloxy, tetramethylpiperidino-N-oxyl and 1-oxyl 2,2,6,6-tetramethyl-4-piperidinol.

4. The vinyl aromatic anti-polymerization composition of claim 3 wherein said nitroxyl free radical compound (B) is 4-hydroxy-2,2,6,6-tetramethyl-1-piperidinyloxy.

5. The vinyl aromatic monomer anti-polymerization composition of claim 1, wherein (A)+(B) collectively are added to the vinyl aromatic monomer in an amount ranging from about 10 to about 150 ppm based upon one million parts of the vinyl aromatic monomer.

6. The vinyl aromatic monomer anti-polymerization composition of claim 1, wherein the composition is in a liquid carrier including water or a non-polar organic solvent.

7. The vinyl aromatic anti-polymerization composition of claim 1 further comprising (C) a retarder compound selected from the group consisting of i) dinitrobutylphenol and ii) a quinone methide.

8. The vinyl aromatic monomer anti-polymerization composition of claim 7, wherein the retarder (C) is added to the vinyl aromatic monomer in an amount ranging from about 50 to about 1500 ppm based upon one million parts of the vinyl aromatic monomer.

9. The vinyl aromatic monomer anti-polymerization composition of claim 7, wherein the retarder (C) is dinitrobutylphenol.

10. The vinyl aromatic monomer anti-polymerization composition of claim 7, wherein the retarder is (C) quinone methide.

* * * * *

UNITED STATES PATENT AND TRADEMARK OFFICE
CERTIFICATE OF CORRECTION

PATENT NO. : 9,206,268 B2  
APPLICATION NO. : 13/235004  
DATED : December 8, 2015  
INVENTOR(S) : Link et al.

Page 1 of 1

It is certified that error appears in the above-identified patent and that said Letters Patent is hereby corrected as shown below:

In the Claims

In Column 5, Line 12, in Claim 1, delete "B)" and insert -- (B) --, therefor.

In Column 5, Line 22, in Claim 4, delete "aromatic" and insert -- aromatic monomer --, therefor.

In Column 6, Line 9, in Claim 7, delete "aromatic" and insert -- aromatic monomer --, therefor.

Signed and Sealed this  
Twenty-sixth Day of July, 2016

Michelle K. Lee  
*Director of the United States Patent and Trademark Office*